(12) United States Patent
Plassman

(10) Patent No.: US 9,198,681 B2
(45) Date of Patent: Dec. 1, 2015

(54) DEVICE AND METHOD FOR REMOVING TISSUE INSIDE A BODY VESSEL

(71) Applicant: COOK MEDICAL TECHNOLOGIES LLC

(72) Inventor: Trevor Plassman, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 129 days.

(21) Appl. No.: 13/650,246

(22) Filed: Oct. 12, 2012

(65) Prior Publication Data

US 2014/0107677 A1    Apr. 17, 2014

(51) Int. Cl.
*A61B 17/22*    (2006.01)
*A61B 17/3207*    (2006.01)
*A61B 17/3205*    (2006.01)

(52) U.S. Cl.
CPC ....... *A61B 17/22031* (2013.01); *A61B 17/3207* (2013.01); *A61B 17/32053* (2013.01); *A61B 2217/005* (2013.01)

(58) Field of Classification Search
CPC .... A61B 17/3207; A61B 17/28; A61B 17/29; A61B 17/22
USPC ......... 606/159, 191, 200, 205–209, 127, 128, 606/114
See application file for complete search history.

(56) References Cited

U.S. PATENT DOCUMENTS

| | | | |
|---|---|---|---|
| 4,290,427 A | 9/1981 | Chin | |
| 4,576,162 A | 3/1986 | McCorkle | |
| 4,896,678 A * | 1/1990 | Ogawa | 600/564 |
| 5,304,189 A | 4/1994 | Goldberg et al. | |
| 5,372,601 A | 12/1994 | Lary | |
| 5,373,840 A * | 12/1994 | Knighton | 600/106 |
| 5,620,415 A * | 4/1997 | Lucey et al. | 604/22 |
| 5,658,302 A | 8/1997 | Wicherski et al. | |
| 5,662,671 A * | 9/1997 | Barbut et al. | 606/170 |
| 5,899,912 A | 5/1999 | Eaves, III | |
| 5,984,939 A * | 11/1999 | Yoon | 606/170 |
| 6,039,748 A * | 3/2000 | Savage et al. | 606/180 |
| 6,383,195 B1 * | 5/2002 | Richard | 606/114 |
| 6,447,489 B1 * | 9/2002 | Peterson | 604/264 |
| 6,958,069 B2 * | 10/2005 | Shipp et al. | 606/127 |
| 2004/0242960 A1 * | 12/2004 | Orban, III | 600/106 |
| 2005/0049633 A1 * | 3/2005 | Watanabe | 606/205 |
| 2006/0235368 A1 * | 10/2006 | Oz | 606/1 |
| 2007/0250096 A1 * | 10/2007 | Yamane et al. | 606/159 |
| 2012/0109171 A1 * | 5/2012 | Zeroni et al. | 606/159 |

* cited by examiner

*Primary Examiner* — Jonathan W Miles
*Assistant Examiner* — George J Ulsh
(74) *Attorney, Agent, or Firm* — Brinks Gilson & Lione

(57) ABSTRACT

An intravascular tissue removal tool has an elongated flexible sheath with a proximal end, a distal end, and a lumen extending from the proximal end to the distal end, the lumen having a distal lumen diameter near the distal end; cutting elements extending into the lumen near the distal end of the flexible sheath; a forceps having an open state and a closed state, and further having an extended position relative to the flexible sheath, in which the forceps is located substantially outside the flexible sheath near the distal end and a retracted position relative to the flexible sheath, in which the forceps is located substantially inside the flexible sheath; and an elongated actuation member being attached to the forceps for switching the forceps between the open state and the closed state and for moving the forceps between the extended state and the retracted state.

10 Claims, 2 Drawing Sheets

DEVICE AND METHOD FOR REMOVING TISSUE INSIDE A BODY VESSEL

TECHNICAL FIELD

The present application relates to a device and a method for removing tissue inside a body vessel. More specifically, the application relates to a fibrin removal tool and a method of removing fibrin from a body vessel.

BACKGROUND

When a blood clot forms in a venous vessel and is left in the vessel for more than about two weeks, it starts forming fibrin strands, so-called synechiae. The fibrin strands do not only contribute to an obstruction of the vessel, but also thicken the vessel walls and thus limit the elasticity of the vessel walls.

It is known to reopen a body vessel by implanting a stent that presses the fibrin strands against the vessel wall. It is further known to remove fibrin strands from vessel walls with fairly complex tools.

SUMMARY

According to a first aspect of the present invention, an intravascular tissue removal tool comprises an elongated flexible sheath with a proximal end, a distal end, and a lumen extending from the proximal end to the distal end, the lumen having a distal lumen diameter near the distal end; cutting elements extending into the lumen near the distal end of the flexible sheath; a forceps having an open state and a closed state, and further having an extended position relative to the flexible sheath in which the forceps is located substantially outside the flexible sheath near the distal end and a retracted position relative to the flexible sheath, in which the forceps is located substantially inside the flexible sheath; and an elongated actuation member extending through the flexible sheath from the proximal end to the forceps, the actuation member being attached to the forceps for switching the forceps between the open state and the closed state and for moving the forceps between the extended state and the retracted state. Because the cutting elements are located on the inside of the removal tool, any risk of injury to the surrounding body vessel wall is reduced.

According to a further aspect of the invention, the tissue removal comprises a tubular ring proximate the distal end of the flexible sheath, the tubular ring carrying the cutting elements. The ring may be made of a harder material than the flexible sheath for durability.

For example, the tubular ring may be inserted into the distal end of the flexible sheath. It may be fastened to the flexible sheath by press-fitting, by adhesive or by any other secure method, for example with a clamping ring or the like. If a tubular ring is provided, the cutting elements may be attached to the tubular ring or may even be unitarily formed with the tubular ring.

According to a further aspect of the invention a method of removing tissue from a body vessel comprises the steps of providing an intravascular tissue removal tool according to the first aspect of the invention; placing the distal end of the flexible sheath in the body vessel near a site selected for tissue removal; distally moving the actuation member relative to the flexible sheath until the forceps occupies the extended position in the open state; switching the forceps from the open state to the closed state to grab tissue for the tissue removal; causing a relative movement between the flexible sheath and the forceps toward the retracted position until the tissue makes contact with the cutting elements; severing the tissue; and proximally removing the tissue.

The relative movement toward the retracted position may be accomplished by moving the flexible sheath relative to the body vessel, or by moving the forceps relative to the body vessel, or both.

According to a further aspect of the invention, the severed tissue may be distally removed though the flexible sheath. Vacuum applied to the flexible sheath from the proximal end may aid the removal of tissue.

DETAILED DESCRIPTION OF THE DRAWINGS

Figure 1A:
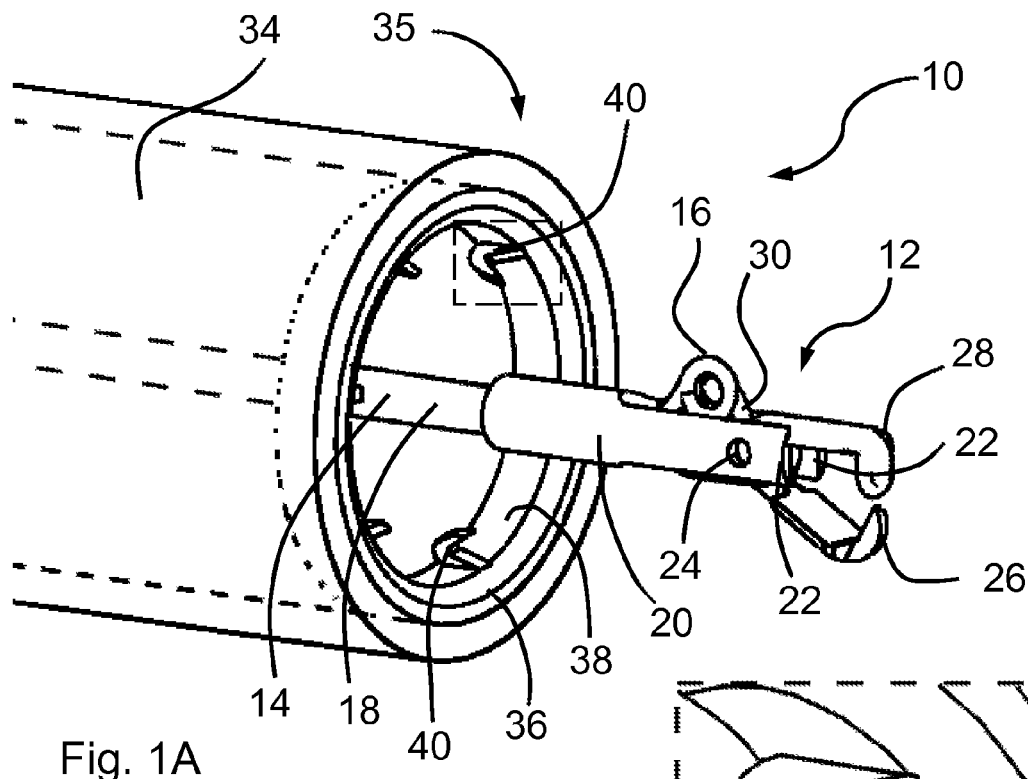
FIG. 1A shows a distal end of an intravascular tissue removal tool according to a first embodiment.

When a blood clot forms in a venous vessel and is left in the vessel for more than about two weeks, it starts forming fibrin strands, so-called synechiae. The fibrin strands do not only contribute to an obstruction of the vessel, but also thicken the vessel walls and thus limit the elasticity of the vessel walls. Thus, the present invention provides a safe way of reopening the vessel by removing fibrin strands while reducing the risk of injury to the vessel walls.

Now referring to FIG. 1, a fibrin removal tool 10 comprises a grip forceps 12 located at the distal end of the fibrin removal tool 10 remotely operable via a wire assembly 14. The wire assembly 14 may, for example, be a push-pull wire assembly with a core wire 16 and a coaxial sleeve 18 arranged around the core wire 16. The sleeve 18 may be rigidly connected to a bearing tube 20 with a bifurcated distal end forming two bearing arms 22 with a bearing hole 24 extending through both bearing arms 22 and defining a hinge axis. In the example shown, the forceps 12 comprises two gripping jaws 26 and 28. Gripping jaw 26 is hingeable about the hinge axis via a hinge pin inserted through the bearing arms 22 and the gripping jaw 26. The gripping jaw 26 is rigidly connected to an actuation lever 30 extending from the hinge axis opposite the gripping jaw 26. The actuation lever 30 is engaged by the core wire 16 for remotely hinging the gripping jaw 26. The other gripping jaw 28 may be rigidly fastened to the bearing tube 20.

The forceps 12 is located outside a distal end 35 of a flexible sheath 34. The flexible sheath 34 preferably has a structure that allows bending and resists kinking. A tubular ring 36 is fixedly connected to the distal end 35 of the flexible sheath. In the embodiment shown in FIG. 1A, the tubular ring 36 is press-fitted into the distal end 32 of flexible sheath 34. Other options include and attachment of the tubular ring 36 with an adhesive or with a positively locking engagement, such as a clamping ring. The tubular ring 36 may also extend axially outward beyond the distal end 35 of the flexible sheath 34 without leaving the scope of the present invention.

The tubular ring 36 has an interior surface 38 that extends in a generally axial direction and defines an internal diameter of the tubular ring 36. A plurality of cutting elements 40 extend from the interior surface 38 inward into the tubular ring 36. FIG. 1A indicates that six of the cutting elements 40 are distributed around the circumference of the interior surface 38. The number of cutting elements 40 may be higher or lower than six and depends on the internal diameter of the tubular ring 36, on the size of the cutting elements 40, and on the task at hand.

Figure 1B:
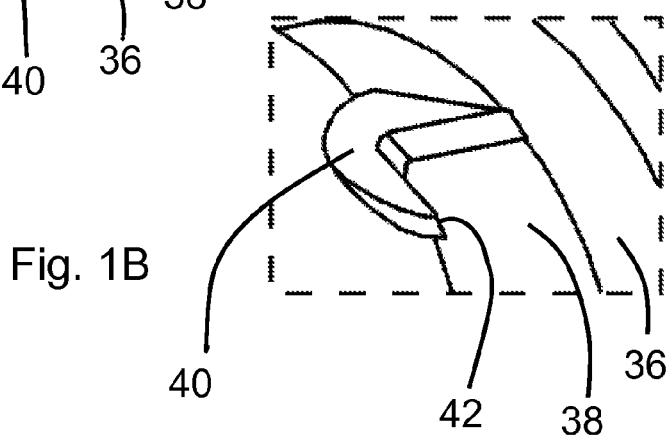
FIG. 1B shows an enlarged detail view of FIG. 1A.

FIG. 1B shows a detail of FIG. 1A and corresponds to the portion indicated by a broken line in FIG. 1A. The cutting element 40 extends generally in a radial plane along the longitudinal axis of the tubular ring 36. The cutting element 40 of FIGS. 1A and 1B is hook-shaped with a tapered end 42 pointing toward the distal end of the flexible sheath 34 and of the tubular ring 36. The cutting element 40 may have one or more sharpened edges forming blades, preferably facing the distal end of the flexible sheath. In the embodiment shown, only the tapered end of the hook operates as a blade. But it is well within the scope of the present invention to sharpen the inside of the hook so as to form a sickle-like blade.

Figure 2:
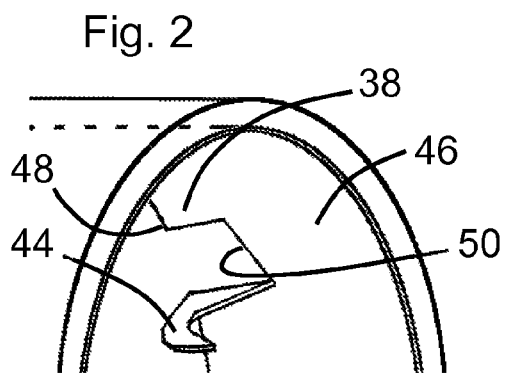
FIG. 2 shows a detail view of a second embodiment of intravascular tissue removal tool.

FIG. 2 depicts an alternative embodiment of a cutting element 44. Cutting element 44 is a unitary portion of the tubular ring 46. Near the proximal end 48, a portion of the tubular ring has been cut and bent inward to form the cutting element 44. Thus, a portion of the interior wall 38 has been replaced by a void. The void may be complementary to the shape of the cutting element or may have a simplified contour. For example, in the embodiment shown in FIG. 2, the contour of the void 50 is a tetragon or generally shaped like a rectangle. The cutting element 44 has a hook shape as previously described in connection with FIGS. 1A and 1B and may have been sharpened along one or more edges.

Figure 3:
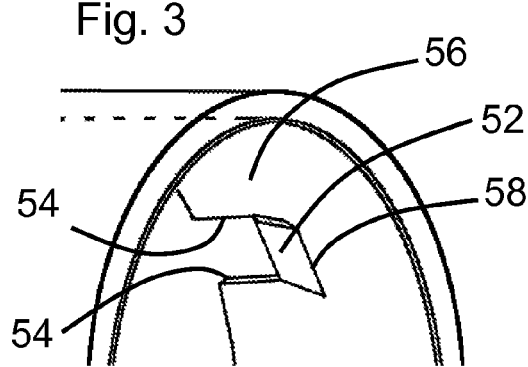
FIG. 3 shows a detail view of a third embodiment of the intravascular tissue removal tool.

In a further alternative embodiment as shown in FIG. 3, a cutting element 52 may be formed by making two axial cuts 54 in the tubular ring 56 that originate at the proximal end of the tubular ring 56 and progress toward the distal end. A tab formed between the axial cuts is bent toward the distal end of the tubular ring 56. The length of the axial cuts 54 is preferably less than half of the axial length of the tubular ring 56 because it is preferred that the cutting elements 52 do not extend beyond the distal end of the tubular ring. In the embodiment shown in FIG. 3, the two axial cuts 54 are aligned generally parallel to each other to form a generally rectangular tab. But they may also form an angle between each other or be curved to give the cutting elements 52 a desired shape. The tab forming cutting element 52 has a sharpened edge facing the distal end of the tubular ring 56 and extending in a generally circumferential direction. While the edge 58 is shows as strait, it may be cured or angled, or even serrated without leaving the scope of the present invention. Such variations are applicable to all embodiments discussed above and below.

The principle of distally folding a portion of the tubular ring 56 to form cutting elements 52 can also be applied without making any axial cuts. Instead, an entire proximal portion of the tubular ring may be folded inward and toward the distal end. The edge of the folded portion may have a varying radius, for example to form a star-shaped or other pattern. Further the edge of the folded portion may be sharpened along its entire length or along portions.

All of the described variations have in common that the cutting elements and all sharpened edges are located inside the lumen of the respective tubular ring or inside the lumen of the flexible sheath where no tubular ring is provided. It is preferred that the cutting elements do not distally extend beyond the distal end of the tubular ring or the flexible sheath, respectively to reduce the risk of undesired injury to vessel walls. When the tissue removal tool is inserted into a body vessel, the vessel walls are protected from any damage by the cutting elements.

For removing tissue, in particular fibrin strands, an operator advances the forceps 12 through the flexible sheath 34 to the targeted fibrin strands. Then the operator causes the forceps 12 to grab a fibrin strand by moving the core wire 16 relative to the sleeve 18 to move the gripping jaw 26 toward the gripping jaw 28. When the forceps holds fibrin strand between the gripping jaws, the operator distally moves the flexible sheath 34 with the tubular ring past the forceps 12. The fibrin strand is pulled inside the lumen of the tubular ring, where the cutting elements sever the fibrin strand.

Optionally, a vacuum may be applied to the flexible sheath from the proximal end thereof. The vacuum can move severed fibrin strand away from the body vessel. Alternatively, the fibrin strand may be distally removed by the forceps 12 or any other mechanical device.

Figure 4:
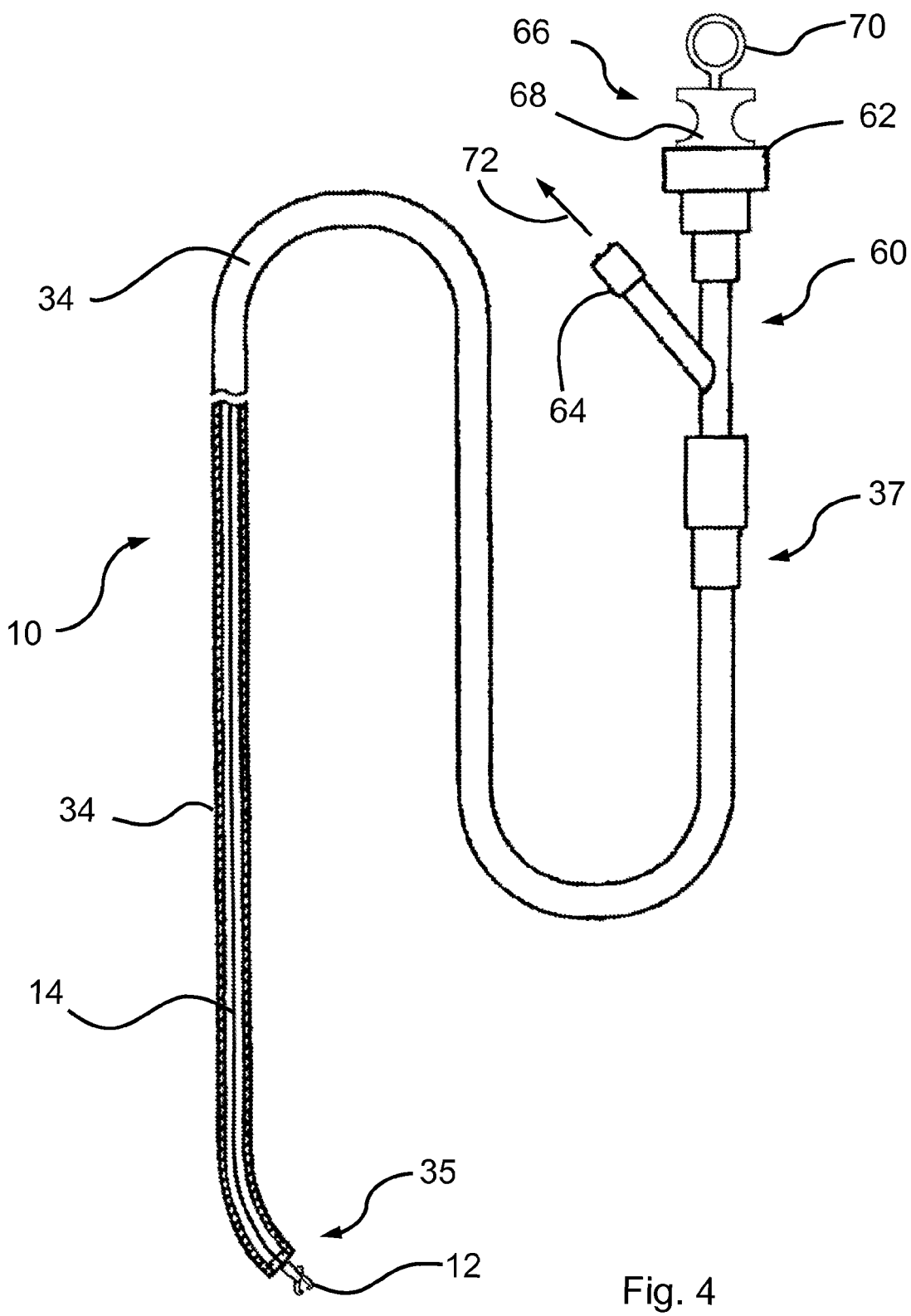
FIG. 4 shows a surgical catheter tool for removing fibrin according to another aspect of the invention.

Now referring to FIG. 4, the tissue removal tool 10 described in several embodiments above is schematically shown in its entirety. The flexible sheath 34 and the wire assembly 14 both have a length sufficient for entering a body vessel and placing the distal end 35 of the flexible sheath near a site where a removal of fibrin strands is desired. The sheath 34 has a proximal end 37 attached to an actuator assembly 60 comprising a plurality of access ports 62 and 64. Only two of the access ports 62 and 64 are shown, but a different number of access ports may be present without leaving the scope of the present invention.

A schematically indicated actuator device 66 is connected to the wire assembly 14, visible in the distal portion of the flexible sheath 34 that is shown in a cross-sectional view. A first actuator element 68 of the actuator device 66 is attached to the sleeve 18, while a second actuator element 70 is connected to the core wire 16. The first and second actuator elements 68 and 70 are axially movable relative to each other so as to actuate the forceps 12 in the previously described manner.

An axial movement of the actuator device 66 distally and proximally relative to the flexible sheath moves to the forceps 12 via the wire assembly 14. Distally moving the actuator assembly relative to the flexible sheath 34 causes the forceps 12 to move distally toward an extended position, in which the forceps is located outside the distal end 35 of the flexible sheath as shown in FIG. 4. In the extended position, the forceps 12 is preferably actuated to grab fibrin strands or other tissue located in the proximity of the forceps 12. Subsequently, the distal end 35 of the flexible sheath 34 is pushed distally over the forceps 12 so that the forceps enters the distal end 35 of the flexible sheath 34. Alternatively, the forceps 12 may be pulled into the distal end 35 of the flexible sheath 34. The grabbed fibrin strand or tissue is then severed by exposing it to the cutting elements 40, 44, or 52. Optionally, a vacuum source 72 may be connected to port 64 for distally transporting any severed fibrin strands or tissue away from the body vessel.

For placing the tissue removal device in the human body, the distal end of the tissue removal device 10 may be inserted via an external catheter in a generally known manner. Suitable materials for cutting elements, forceps jaws, and forceps wire are steel or another suitable metal. The sheath may be manufactured of a polymer that may optionally be supported by a braided or coiled wire. Typical dimensions of the sheath may range from about 4 French up to about 18 French, depending on the intended application. To reduce adherence of the outside of the fibrin removal device to the vessel walls and to the tissue, coatings may be applied before assembly. One suitable coating is, for example, PTFE.

While the foregoing description made reference to fibrin strands and cutting thereof, the invention is not limited to such a use and is suited for taking biopsy samples or for any cutting of intravascular tissue with a reduced risk of damaging the vessel wall.

The foregoing description of various embodiments of the invention has been presented for purposes of illustration and description. It is not intended to be exhaustive or to limit the invention to the precise embodiments disclosed. Numerous modifications or variations are possible in light of the above teachings, and the properties of one embodiment may be modified with properties of another. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An intravascular tissue removal tool comprising: an elongated flexible sheath with a proximal end, a distal end, and a lumen extending from the proximal end to the distal end, the lumen having a distal lumen diameter near the distal end; a plurality of cutting elements fixedly attached to the flexible sheath and extending inward into the lumen near the distal end of the flexible sheath, each of the cutting elements having a sharpened edge extending in a circumferential direction and pointed towards the distal end of the flexible sheath; a forceps having an open state and a closed state, and further having an extended position relative to the flexible sheath, in which the forceps is located substantially outside the flexible sheath near the distal end and a retracted position relative to the flexible sheath, in which the forceps is located substantially inside the flexible sheath; and an elongated actuation member extending through the flexible sheath from the proximal end to the forceps, the actuation member being attached to the forceps for switching the forceps between the open state and the closed state and for moving the forceps between the extended state and the retracted state.

2. The tissue removal tool of claim 1, wherein the cutting elements are circumferentially distributed.

3. The tissue removal tool of claim 1, further comprising a tubular ring proximate the distal end of the flexible sheath, the tubular ring carrying the cutting elements.

4. The tissue removal tool of claim 3, wherein the tubular ring is inserted into the distal end of the flexible sheath.

5. The tissue removal tool of claim 3, wherein the cutting elements are attached to the tubular ring.

6. The tissue removal tool of claim 3, wherein the cutting elements are unitarily formed with the tubular ring.

7. The tissue removal tool of claim 1, wherein the actuation member comprises a wire assembly with a sleeve and a core wire.

8. An intravascular tissue removal tool comprising:
an elongated flexible sheath with a proximal end, a distal end, and a lumen extending from the proximal end to the distal end, the lumen having a distal lumen diameter near the distal end;
cutting elements fixedly attached to the flexible sheath and extending inward into the lumen near the distal end of the flexible sheath, each of the cutting elements having a sharpened edge extending in a circumferential direction, each of the cutting elements being unitarily formed with a tubular ring proximate the distal end of the flexible sheath by at least one cut in the tubular ring, the at least one cut originating at the proximal end of the tubular ring, the cutting elements being bent radially inward into the tubular ring;
a forceps having an open state and a closed state, and further having an extended position relative to the flexible sheath, in which the forceps is located substantially outside the flexible sheath near the distal end and a retracted position relative to the flexible sheath, in which the forceps is located substantially inside the flexible sheath; and
an elongated actuation member extending through the flexible sheath from the proximal end to the forceps, the actuation member being attached to the forceps for switching the forceps between the open state and the closed state and for moving the forceps between the extended state and the retracted state.

9. The tissue removal tools of claim 8, wherein each of the cutting elements is formed by a tab between two axial cuts originating at the proximal end of the tubular ring, the tab being bent toward the distal end of the tubular ring.

10. An intravascular tissue removal tool comprising:
an elongated flexible sheath with a proximal end, a distal end, and a lumen extending from the proximal end to the distal end, the lumen having a distal lumen diameter near the distal end;
cutting elements fixedly attached to the flexible sheath and extending inward into the lumen near the distal end of the flexible sheath, each of the cutting elements being hook-shaped with a tip of the hook pointing to the distal end of the flexible sheath and having a sharpened edge extending in a circumferential direction;
a forceps having an open state and a closed state, and further having an extended position relative to the flexible sheath, in which the forceps is located substantially outside the flexible sheath near the distal end and a retracted position relative to the flexible sheath, in which the forceps is located substantially inside the flexible sheath; and
an elongated actuation member extending through the flexible sheath from the proximal end to the forceps, the actuation member being attached to the forceps for switching the forceps between the open state and the closed state and for moving the forceps between the extended state and the retracted state.

* * * * *